(12) United States Patent
Mallard

(10) Patent No.: US 10,695,315 B2
(45) Date of Patent: Jun. 30, 2020

(54) COMPOSITION COMPRISING AVERMECTIN COMPOUNDS WITHOUT GELLING AGENTS

(71) Applicant: Nestlé Skin Health SA, Lausanne (CH)

(72) Inventor: Claire Mallard, Mougins (FR)

(73) Assignee: NESTLÉ SKIN HEALTH S.A., Lausanne (CH)

( * ) Notice: Subject to any disclaimer, the term of this patent is extended or adjusted under 35 U.S.C. 154(b) by 0 days.

(21) Appl. No.: 16/463,804

(22) PCT Filed: Nov. 23, 2017

(86) PCT No.: PCT/EP2017/080147
§ 371 (c)(1),
(2) Date: May 23, 2019

(87) PCT Pub. No.: WO2018/096009
PCT Pub. Date: May 31, 2018

(65) Prior Publication Data
US 2019/0282539 A1    Sep. 19, 2019

(30) Foreign Application Priority Data

Nov. 24, 2016 (EP) ..................................... 16306556

(51) Int. Cl.
| | |
|---|---|
| A61K 9/107 | (2006.01) |
| A61K 31/351 | (2006.01) |
| A61P 17/00 | (2006.01) |
| A61K 9/00 | (2006.01) |
| A61K 9/06 | (2006.01) |
| A61P 17/10 | (2006.01) |
| A61K 9/10 | (2006.01) |
| A61K 31/7048 | (2006.01) |

(52) U.S. Cl.
CPC .......... *A61K 31/351* (2013.01); *A61K 9/0014* (2013.01); *A61K 9/06* (2013.01); *A61K 9/10* (2013.01); *A61K 9/107* (2013.01); *A61K 31/7048* (2013.01); *A61P 17/00* (2018.01); *A61P 17/10* (2018.01)

(58) Field of Classification Search
None
See application file for complete search history.

(56) References Cited

U.S. PATENT DOCUMENTS

| | | | |
|---|---|---|---|
| 5,773,422 | A | 6/1998 | Komer |
| 8,858,967 | B2 | 10/2014 | Astruc et al. |
| 2005/0143325 | A1 | 6/2005 | Guzzo et al. |
| 2006/0100165 | A1 | 5/2006 | Manetta et al. |
| 2007/0116731 | A1 | 5/2007 | Astruc et al. |
| 2008/0214657 | A1 | 9/2008 | Spring et al. |
| 2009/0035338 | A1* | 2/2009 | Segura-Orsoni ..... A61K 9/0014 424/401 |
| 2009/0233877 | A1 | 9/2009 | Kaoukhov et al. |
| 2009/0264378 | A1 | 10/2009 | Kaoukhov et al. |
| 2010/0093652 | A1* | 4/2010 | Spring ................. A61K 9/0014 514/32 |
| 2012/0004200 | A1 | 1/2012 | Nadau-Fourcade et al. |
| 2013/0108563 | A1 | 5/2013 | Diaz-Astruc et al. |
| 2015/0105340 | A1 | 4/2015 | Spring et al. |
| 2016/0303152 | A1 | 10/2016 | Nayar |
| 2016/0303154 | A1 | 10/2016 | Nayar |
| 2016/0303155 | A1 | 10/2016 | Nayar |

FOREIGN PATENT DOCUMENTS

| | | |
|---|---|---|
| FR | 2 924 944 A1 | 6/2009 |
| WO | WO-2016/022066 A1 | 2/2016 |
| WO | WO-2016/024855 A1 | 2/2016 |

OTHER PUBLICATIONS

International Search Report issued in PCT/EP2017/080146 and dated Jan. 30, 2018.
International Search Report issued in PCT/EP2017/080147 and dated Jan. 24, 2018.
International Search Report issued in PCT/EP2017/080148 and dated Feb. 6, 2018.

* cited by examiner

*Primary Examiner* — Robert A Wax
*Assistant Examiner* — Melissa S Mercier
(74) *Attorney, Agent, or Firm* — Foley & Lardner LLP; Sunit Talapatra

(57) ABSTRACT

The invention relates to a dermatological or pharmaceutical composition comprising at least one aqueous phase, at least one fatty phase comprising one or more fatty compounds and at least one active phase comprising one or more active compounds chosen from avermectin compounds and one or more solvents and/or propenetrating agents of avermectin compounds, where the composition does not comprise gelling agent.

The invention relates also to the composition for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea.

Finally, the invention relates to a method for preparing the composition.

22 Claims, No Drawings

COMPOSITION COMPRISING AVERMECTIN COMPOUNDS WITHOUT GELLING AGENTS

CROSS-REFERENCE TO RELATED APPLICATIONS

This application is a National Phase of International Patent Application No. PCT/EP2017/080147, filed Nov. 23, 2017, published on May 31, 2018 as WO 2018/096009 A1, which claims priority to European Patent Application No. 16306556.8, filed Nov. 24, 2016. The contents of these applications are herein incorporated by reference in their entirety.

The invention relates to a dermatological or pharmaceutical composition comprising at least one active compound chosen from avermectin compounds without gelling agent.

In particular, the invention relates to a dermatological or pharmaceutical composition comprising at least one aqueous phase, at least one fatty phase comprising one or more fatty compounds and at least one active phase comprising one or more active compounds chosen from avermectin compounds and one or more solvents and/or propenetrating agents of avermectin compounds, where the composition does not comprise gelling agent.

The invention relates also to the composition for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea.

Finally, the invention relates to a method for preparing the composition.

The class of avermectins, a group of macrocyclic lactones produced by the bacterium *Streptomyces avermitilis* (Reynolds JEF (Ed) (1993) Martindale, The extra pharmacopoeia, $29^{th}$ Edition, Pharmaceutical Press, London), namely includes ivermectin, invermectin, avermectin, abamectin, doramectin, eprinomectin, and selamectin.

In particular, ivermectin is a mixture of two compounds, 5-O-demethyl-22,23-dihydroavermectin $A_{1a}$ and 5-O-demethyl-22-23-dihydroavermectin $A_{1b}$.

In the middle of the 1980s, ivermectin was presented as a broad-spectrum anti-parasitic medicinal product for veterinary use (W. C. CAMPBELL, et al., (1983) "Ivermectin: a potent new anti-parasitic agent", Science, 221, 823-828). It is effective against most common intestinal worms (except tapeworms), most acarids and some lice. It in particular exhibits considerable affinity for the glutamate-dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand-dependent chloride channels, such as those involving the neuromediator GABA (gamma-aminobutyric acid).

Ivermectin is more particularly an anthelmintic. It has been administered in humans in the treatment of onchocerciasis caused by *Onchocerca volvulus*, of gastrointestinal strongyloidias (anguillulosis) and of human scabies and also in the treatment of microfilaremia diagnosed or suspected in individuals suffering from lymphatic filariosis due to *Wuchereria bancrofti*.

More recently, compounds of avermectin family have been used in the treatment of dermatological conditions such as rosacea in a topical pharmaceutical composition suited for human administration.

For example, the document US 2006/0100165 describes the use of topical compositions comprising ivermectin for the treatment of dermatological conditions such as rosacea.

The compositions disclosed in this document are in the form of a cream and are chemically and physically stable over time thanks to the presence of a gelling agent. However, the manufacturing process requires high shearing energy to disperse the gelling agent and to homogenize the cream at the end of the process due to its high consistency.

Consequently, this formulation is also difficult to pump.

Therefore, there is a need to provide compositions comprising avermectin compounds, especially ivermectin, which do not require high shearing energy to manufacture and are easy to pump without impeding their chemical and physical stability over time.

It has now been found, surprisingly, that a dermatological or pharmaceutical composition comprising at least one active compound chosen from avermectin compounds without gelling agents presents a lower viscosity while having good chemical and physical stability over time.

The present invention thus concerns a dermatological or pharmaceutical composition comprising at least one aqueous phase, at least one fatty phase comprising one or more fatty compounds and at least one active phase comprising one or more active compounds chosen from avermectin compounds and one or more solvents and/or propenetrating agents of avermectin compounds, where the composition does not comprise gelling agent.

The composition according to the invention is preferably in the form of a cream but presents a lower viscosity and a low flow threshold.

Hence, the composition according to the invention is sprayable using either a mechanic pump spray or a pressurized spray.

In addition, the composition according to the invention exhibits good chemical and physical stability over time, even at a temperature above ambient temperature (for example, 40° C.), especially over a period of at least two to three months.

"Chemical stability" means that the avermectin compounds amount of the composition does not change more than 5% by weight relative to the initial amount in avermectin compounds of the composition.

"Physical stability" means that the composition meets the acceptance criteria for appearance, physical attributes and functionality test (e.g. color, phase separation, dose delivery per actuation). More precisely the physical stability means that at least two of the following criteria, preferably all of the following criteria: microscopic aspect, macroscopic aspect, viscosity and pH, do not significantly vary after manufacture time during 1 month, preferably during 2 months and even more preferably during 3 months.

The present invention also concerns the dermatological or pharmaceutical composition as defined above for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea.

The invention concerns also a method for preparing the composition comprising the following steps:

a) mixing the fatty substances in order to form the fatty phase, b) mixing the constituents of the aqueous phase in order to form the aqueous phase, c) mixing the avermectin compounds and the other constituents of the active phase in order to form the active phase, then d) incorporating the fatty phase into the aqueous phase so as to form a emulsion, then e) incorporating the active phase into the emulsion so as to form the composition.

The manufacturing process is improved with a reduced time of manufacture and a lower energy needed to achieve the formulation.

According to the present invention, "active phase" refers to the phase comprising the active compound.

Other subject-matters, characteristics, aspects and advantages of the invention will become even more clearly apparent on reading the description and the examples which follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

As described above, the composition according to the invention does not comprise gelling agents.

According to the invention, a gelling agent is any substance added to a composition to increase the viscosity of said composition, the gelling agent representing from 0.01% to 4% by weight, more preferably from 0.01% to 1% by weight relative to the total weight of the composition. By increasing or modifying the viscosity the composition is more stable over time and physical instabilities such as phase separation, flocculation and creaming do not occur.

The gelling agent or agents are preferably chosen from carboxyvinyl polymers (carbomers), cellulose derivatives, xanthane gums, aluminium/magnesium silicates, guar gums, polyacrylamides, modified starches, and mixtures thereof.

As carboxyvinyl polymer (carbomer), mention may be made of carbomer, Carbopol 981, Carbopol ETD 2020, Carbopol 980, Carbopol Ultrez 10 NF and Pemulen TR1, marketed by Lubrizol.

More preferably, as carboxyvinyl polymers, mention may be made of acrylates/$C_{10-30}$ alkyl acrylate crosspolymer (Pemulen TR1).

As cellulose derivative, mention may be made of hydroxypropylmethylcellulose and hydroxyethylcellulose.

As aluminium/magnesium silicate, mention may be made of Veegum K and Veegum Ultra marketed by Vanderbilt.

As polyacrylamide, mention may be made of the mixture polyacrylamide/C13-14 isoparaffin/laureth-7, for instance that marketed by SEPPIC under the name Sepigel 305 and the mixture acrylamide, AMPS copolymer dispersion 40%/isohexadecane under the name Sepineo P600.

As modified starch, mention may be made of Structures Solanace marketed by Akzo Nobel.

Thus, the dermatological or pharmaceutical composition according to the invention preferably comprises none of these compounds, that is to say the dermatological or pharmaceutical composition according to the invention preferably does not comprise carboxyvinyl polymers (carbomers), cellulose derivatives, xanthane gums, aluminium/magnesium silicates, guar gums, polyacrylamides and modified starches.

The avermectin compounds that are used according to the invention are preferably chosen from ivermectin, invermectin, avermectin, abamectin, doramectin, eprinomectin and selamectin.

Preferably, the avermectin compound is ivermectin.

The composition according to the invention comprises preferably from 0.01 to 10% by weight, more preferably from 0.1 to 5% by weight of avermectin compounds, relative to the total weight of the composition.

The dermatological or pharmaceutical composition according to the invention comprises at least one solvent and/or propenetrating agent of avermectin compounds.

A solvent of avermectin compounds is defined as a liquid compound in which the compounds of the avermectin family, in particular ivermectin, have a solubility at room temperature and at atmospheric pressure of more than or equal to 2% by weight relative to the composition comprising only said solvent or said solvent in association with one or more solvents of avermectin compounds.

Solubility of a compound into one or more solvents is defined as the amount of compound that passes into a solution constituted of the one or more solvents to achieve a saturated solution at constant temperature and pressure (stirring of the saturated solution from 16 to 24 hours). Solubility is expressed in terms of maximum volume or mass of the compound that dissolves in a given volume or mass of one or more solvents.

A propenetrating agent of avermectin compounds makes it possible to facilitate the penetration of the compounds of the avermectin family into the skin, preferably dissolves said compounds present in the composition according to the invention.

Preferably, solvents and propenetrating agents of avermectin compounds are chosen from propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, polypropylene glycol-15 stearyl ether ("PPG-15 stearyl ether"), octyl dodecanol, ethyl oleate, $C_{12}$-$C_{15}$ alkyl benzoate and mixtures thereof.

In a preferred embodiment, solvents and propenetrating agents of avermectin compounds are chosen from propylene glycol, oleyl alcohol and mixture thereof.

The dermatological or pharmaceutical composition according to the invention preferably comprises from 1 to 10% by weight, preferably from 3 to 7% by weight of solvents and propenetrating agents of avermectin compounds, relative to the total weight of the composition.

The dermatological or pharmaceutical composition according to the invention preferably comprises one or more fatty compounds.

Preferably, the fatty substances are chosen from vegetable, mineral, animal or synthetic oils, silicone oils, fatty acids, fatty alcohols, waxes, gums, and mixtures thereof.

As an example of a mineral oil, mention may be made, for example, of paraffin oils of various viscosities, such as Primol 352, Marcol 82 or Marcol 152 marketed by IMCD.

As a vegetable oil, mention may be made of sweet almond oil, palm oil, soybean oil, sesame oil and sunflower oil.

As an animal oil, mention may be made of lanolin, squalene, fish oil and mink oil.

As a synthetic oil, mention may be made of fatty acid alcohol esters, such as cetearyl isononanoate marketed in particular under the name Cetiol SN by BASF, isopropyl palmitate, for instance the product marketed under the name Crodamol IPP by Croda, or caprylic capric triglyceride such as Miglyol 812 marketed by IMCD.

As a silicone oil, mention may be made of a dimethicone, such as the product marketed under the name Dow Corning 200 fluid, or a cyclomethicone, such as the product marketed under the name Dow Corning 244 fluid by Dow Corning, or the product marketed under the name Mirasil CM5 by Bluestar Silicones.

As fatty acid, mention may be made of stearic acid.

As a fatty alcohol, mention may be made of stearyl alcohol, cetostearyl alcohol and cetyl alcohol.

As wax, mention may be made of beeswax, carnauba wax and candelilla wax.

As gum, mention may be made of silicone gums.

More preferably, said fatty compounds are chosen from fatty acid alcohol esters, silicone oils, fatty alcohols, and mixtures thereof.

The dermatological or pharmaceutical composition according to the invention may comprise from 5 to 30% by weight, preferably from 10 to 20% by weight of fatty compounds, relative to the total weight of the composition.

The composition according to the invention may comprise one or more surfactants.

Preferably, the surfactants are chosen from non-ionic surfactants.

More preferably the surfactants are chosen from polyoxyethylenated fatty alcohol ethers, sorbitan esters, and mixtures thereof.

As a polyoxyethylenated fatty alcohol ether, mention may be made of ceteareth-20.

As a sorbitan esters, mention may be made of sorbitan monostearate.

The dermatological or pharmaceutical composition according to the invention may comprise from 0.1 to 10% by weight, preferably from 1 to 7% by weight of surfactants, relative to the total weight of the composition.

The aqueous phase of the composition according to the invention comprises water.

The composition according to the invention may also contain inert additives or combinations of these additives, such as flavor enhancers; preservatives; stabilizers; humidity regulators; pH regulators; osmotic pressure modifiers; UV-A and UV-B screening agents; and antioxidants.

Of course, one skilled in this art will take care to choose the optional compound(s) to be added to the composition of the invention in such a way that the advantageous properties intrinsically associated with the present invention are not, or are not substantially, altered by the envisaged addition.

These additives may be present in the composition from 0.001 to 20% by weight relative to the total weight of the composition.

According to one embodiment, the composition according to the invention has a viscosity ranging from 1000 cP to 10000 cP at room temperature using a Brookfield RV.

According to one embodiment, the composition according to the invention has a yield stress ranging from 10 Pa to 80 Pa at room temperature using a Malvern rheometer.

Preferably, the composition according to the invention is suited for treating the skin and can be in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases.

It may also be in the form of suspensions of microspheres or nanospheres or of lipid or polymeric vesicles or of polymeric patches and of hydrogels for controlled release.

More preferably, the composition according to the invention is in cream form.

The composition according to the invention comprises preferably from 5 to 85% of fatty phase, from 5 to 94.9% of aqueous phase, and from 0.1 to 10% of active phase, preferably said composition comprises from 5 to 30% of fatty phase, from 69 to 94% of aqueous phase and from 1 to 7% of active phase.

The pH will preferably range from 5.0 to 7.0, more preferably from 6.0 to 6.5.

Verification of the natural pH of the mixture and possible correction with a solution of a neutralizing agent, and also the incorporation of the optional additives, may be carried out, according to their chemical nature, during one of the steps of the method of preparation, described below.

In a particular embodiment, the composition according to the invention comprises:
  at least one fatty phase comprising from 5 to 30% by weight, preferably from 10 to 20% by weight of fatty compounds, relative to the total weight of the composition, of fatty compounds,
  at least one aqueous phase,
  at least one active phase comprising from 0.01 to 10% by weight, preferably from 0.1 to 5% by weight and from 1 to 10% by weight, preferably from 3 to 7% by weight of solvents and propenetrating agents of avermectin compounds,
  where the composition does not comprise gelling agents.

More preferably in this embodiment, the composition according to the invention comprises:
  at least one fatty phase comprising from 5 to 30% by weight, preferably from 10 to 20% by weight of fatty compounds, relative to the total weight of the composition, of fatty compounds,
  at least one aqueous phase,
  at least one active phase comprising from 0.01 to 10% by weight, preferably from 0.1 to 5% by weight and from 1 to 10% by weight, preferably from 3 to 7% by weight of solvents and propenetrating agents of avermectin compounds,
  where the composition does not comprise carboxyvinyl polymers (carbomers), cellulose derivatives, xanthane gums, aluminium/magnesium silicates, guar gums, polyacrylamides and modified starches.

According to this embodiment, avermectin compound is preferably ivermectin.

According to this embodiment, the composition preferably comprises one or more surfactants.

The dermatological or pharmaceutical composition according to the invention is preferably a topical composition.

This composition according to the invention is useful to treat dermatological conditions/afflictions.

In particular, the composition according to the invention is useful for the treatment of rosacea, of common acne, of seborrheic dermatitis, of perioral dermatitis, of acneiform rashes, of transient acantholytic dermatosis, of acne necrotica miliaris and of atopic dermatitis.

More particularly, the dermatological or pharmaceutical composition is used in the treatment of rosacea.

In a particular embodiment, the composition according to the invention is useful in a method for the treatment of rosacea characterized in that the composition is administered topically.

The present invention also features a method for preparing the composition which comprises the following step:
  a) mixing the fatty substances in order to form the fatty phase, b) mixing the constituents of the aqueous phase in order to form the aqueous phase, c) mixing the avermectin compounds and the other constituents of the active phase in order to form the active phase, then d) incorporating the fatty phase into the aqueous phase so as to form a emulsion, then e) incorporating the active phase into the emulsion so as to form the composition.

In order to illustrate the present invention and the advantages thereof, the following specific examples of compositions comprising ivermectin and the physical and chemical stability thereof are given, it being understood that same are intended only as illustrative and in nowise limitative. In said examples to follow, all parts and percentages are given by weight, unless otherwise indicated.

EXAMPLES

1) Preparation of the Compositions

The comparative composition 1 and the composition 2 according to the invention are formulated according to the following procedure:

In a first beaker, weight the components of the aqueous phase including Pemulen TR1 when present into the composition, heat to 65° C. (±2° C.) and mix all the aqueous phase.

In a second beaker, weigh the fatty phase, heat to 65° C. (±2° C.) and mix all the fatty phase.

When the fatty phase and aqueous phase are at 65° C. (±2° C.), introduce the fatty phase into the aqueous phase then cool.

Allow the emulsion to cool to 50° C. (±2° C.).

In a third beaker, solubilize the avermectin compounds in the active phase at 50° C. (±2° C.) then add this mixture to the preceding obtained emulsion.

Allow the emulsion to cool to 35° C. (±2° C.) with a temperature plateau at 45° C. during 15 minutes with a constant low stirring.

Adjust the pH to 6.0 with the sodium hydroxide solution then cool the emulsion to room temperature.

|  | Ingredients | 1 (comp.) | 2 (inv.) |
|---|---|---|---|
|  |  | % by weight relative to the total weight of the composition | |
| Fatty phase | Isopropyl palmitate | 4.0 | 4.0 |
|  | Cetyl alcohol | 3.5 | 3.5 |
|  | Stearyl alcohol | 2.5 | 2.5 |
|  | Ceteareth-20 | 3.0 | 3.0 |
|  | Sorbitan monostearate | 2.0 | 2.0 |
|  | Dimethicone | 0.5 | 0.5 |
|  | Propyl parahydroxybenzoate | 0.1 | 0.1 |
| Aqueous phase | Pemulen TR1 | 0.2 | — |
|  | Glycerin | 4.0 | 4.0 |
|  | Methyl parahydroxybenzoate | 0.2 | 0.2 |
|  | Disodium EDTA | 0.05 | 0.05 |
|  | Citric acid | 0.05 | 0.05 |
|  | Phenoxyethanol | 1.0 | 1.0 |
|  | Purified water | qs 100 | qs 100 |
| Active phase | Propylene glycol | 2.0 | 2.0 |
|  | Oleyl alcohol | 2.0 | 2.0 |
|  | Ivermectin | 1.0 | 1.0 |
|  | 10% sodium hydroxide | qs pH | qs pH |

2) Physical and Chemical Stability of the Composition

Physical characteristics of the compositions at room temperature (initial time T0)

|  | Composition | |
|---|---|---|
|  | 1 | 2 |
| Macroscopic aspect | white to pale yellowish cream | white cream |
| Microscopic aspect | droplets from 2.5 to 15 µm with presence of refringences | droplets from from 1 to 3 µm with presence of refringences |
| pH | 6.30 | 6.15 |
| Viscosity (cP) | 52267 | 3167 |
| Yield stress (Pa) | 142 | 34 |
| Centrifugation test (5000 rpm 20 mn) | no phase separation | no phase separation |
| Ivermectin titer (%/label claim) | 100.0% | 98.3% |

The viscosity is measured by the use of a Brookfield Viscometer (RV dvII+Small sample adaptator Spindle 34 (for composition 1) or Spindle 21 (for composition 2) v=6 rpm).

The Yield stress is measured by the use of a Rheometer CV0100 Malvern (Cone Plan CP4° 40 mm) with a controlled stress sweep from 0.03 up to 300 Pa.

The composition 2 according to the invention without gelling agent has a lower viscosity at T0 and a lower yield stress than the comparative composition 1.

In addition the composition 2 according to the invention is stable after manufacturing at lab-scale (no phase separation at the centrifugation test) even though it does not contain gelling agent.

Moreover, the droplet size of the composition 2 is finer and more homogenous without gelling agent.

Physical Stability

The table below represents physical stability of the composition 2 according to the invention at 5° C. and room temperature (RT) during three months.

|  | 1 month | | 2 months | | 3 months | |
|---|---|---|---|---|---|---|
| Composition 2 | 5° C. | RT | 5° C. | RT | 5° C. | RT |
| Macroscopic aspect | No change relative to T0 | No change relative to T0 | No change relative to T0 | | | |
| Microscopic aspect | No change relative to T0 | No change relative to T0 | No change relative to T0 | | | |
| pH | 6.19 | 6.20 | 6.11 | 6.13 | 6.03 | 6.10 |
| Viscosity (cP) | 3658 | 3800 | 3267 | 4258 | 3700 | 3692 |

The viscosity is measured by the use of a Brookfield Viscometer (RV dvII+Small sample adaptator Spindle 21 v=6 rpm).

The composition 2 according to the invention is physically stable three months at 5° C. and room temperature (RT) with a constant viscosity value.

No phase separation is observed and ivermectin remains solubilized over time, no crystals formation.

Chemical Stability

The table below represents chemical stability of the composition 2 according to the invention at room temperature (RT) and 40° C. during 3 months.

| Ivermectin titer (%/label claim) |  | Composition 2 |
|---|---|---|
| 2 months | RT | 100.7 (CV 0.0%) |
|  | 40° C. | 101.2 (CV 0.1%) |

| Ivermectin titer (%/label claim) | | Composition 2 |
| --- | --- | --- |
| 3 months | RT | 98.9 (CV 1.1%) |
| | 40° C. | 102.6 (CV 0.9%) |

CV: Coefficient variation

Composition 2 is chemically stable three months at room temperature and 40° C.

The invention claimed is:

1. A dermatological or pharmaceutical composition, comprising:
    (a) 69% to 94% by weight, relative to the total weight of the composition, of at least one aqueous phase;
    (b) 5% to 30% by weight, relative to the total weight of the composition, of at least one fatty phase comprising one or more fatty compounds; and
    (c) 0.1% to 10% by weight, relative to the total weight of the composition, of at least one active phase comprising one or more active compounds selected from avermectin compounds and one or more solvents and/or propenetrating agents of avermectin compounds,
    wherein the composition does not comprise a gelling agent selected from the group consisting of carboxyvinyl polymers, cellulose derivatives, xanthan gums, aluminium/magnesium silicates, guar gums, polyacrylamides, modified starches, and mixtures thereof.

2. The dermatological or pharmaceutical composition according to claim 1, wherein the composition does not comprise any gelling agent.

3. The dermatological or pharmaceutical composition according to claim 1, wherein the one or more avermectin compounds are selected from ivermectin, invermectin, avermectin, abamectin, doramectin, eprinomectin and selamectin.

4. The dermatological or pharmaceutical composition according to claim 3, wherein the avermectin compound is ivermectin.

5. The dermatological or pharmaceutical composition according to claim 1, comprising 0.01 to 10% by weight of avermectin compounds, relative to the total weight of the composition.

6. The dermatological or pharmaceutical composition according to claim 5, comprising 0.1 to 5% by weight of avermectin compounds, relative to the total weight of the composition.

7. The dermatological or pharmaceutical composition according to claim 1, wherein the solvents and/or propenetrating agents of avermectin compounds are selected from propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, polypropylene glycol-15 stearyl ether ("PPG-15 stearyl ether"), octyl dodecanol, ethyl oleate, C12-C15 alkyl benzoate and mixtures thereof.

8. The dermatological or pharmaceutical composition according to claim 1, comprising from 1 to 10% by weight of the solvents and propenetrating agents of avermectin compounds, relative to the total weight of the composition.

9. The dermatological or pharmaceutical composition according to claim 8, comprising from 3 to 7% by weight of the solvents and/or propenetrating agents of avermectin compounds, relative to the total weight of the composition.

10. The dermatological or pharmaceutical composition according to claim 1, wherein the fatty compounds are selected from vegetable, mineral, animal or synthetic oils, silicone oils, fatty acids, fatty alcohols, waxes, gums, and mixtures thereof.

11. The dermatological or pharmaceutical composition according to claim 1, wherein the fatty compounds are selected from fatty acid alcohol esters, silicone oils, fatty alcohols, and mixtures thereof.

12. The dermatological or pharmaceutical composition according to claim 1, comprising 5 to 30% by weight of fatty compounds, relative to the total weight of the composition.

13. The dermatological or pharmaceutical composition according to claim 12, comprising 10 to 20% by weight of fatty compounds, relative to the total weight of the composition.

14. The dermatological or pharmaceutical composition according to claim 1, further comprising one or more surfactants.

15. The dermatological or pharmaceutical composition according to claim 14, wherein the surfactants are selected from non-ionic surfactants.

16. The dermatological or pharmaceutical composition according to claim 14, wherein the surfactants are selected from polyoxyethylenated fatty alcohol ethers, sorbitan esters, and mixtures thereof.

17. A method of treating rosacea, common acne, seborrheic dermatitis, perioral dermatitis, acneiform rashes, transient acantholytic dermatosis, acne necrotica miliaris and/or atopic dermatitis, the method comprising administering a dermatological or pharmaceutical composition according to claim 1.

18. The method according to claim 17 for the treatment of rosacea.

19. The method according to claim 18, wherein the composition is administered topically.

20. A method for preparing the composition according to claim 1, comprising:
    (a) mixing the fatty substances in order to form the fatty phase, wherein the fatty phase is present at a concentration of 5% to 30% by weight, relative to the total weight of the composition;
    (b) mixing the constituents of the aqueous phase in order to form the aqueous phase, wherein the aqueous phase is present at a concentration of 69% to 94% by weight, relative to the total weight of the composition;
    (c) mixing the avermectin compounds and the other constituents of the active phase in order to form the active phase, wherein the active phase is present at a concentration of 0.1% to 10% by weight, relative to the total weight of the composition;
    (d) incorporating the fatty phase into the aqueous phase so as to form an emulsion; and
    (e) incorporating the active phase into the emulsion so as to form the composition.

21. The dermatological or pharmaceutical composition of claim 1, wherein the composition has a viscosity from 1,000 cP to 10,000 cP at room temperature.

22. The dermatological or pharmaceutical composition of claim 1, wherein the composition has a yield stress from 10 Pa to 80 Pa at room temperature.

* * * * *